United States Patent [19]

Nüsslein et al.

[11] 4,169,718

[45] Oct. 2, 1979

[54] 2-(DIMETHYLCARBAMOYLIMINO)-1,3,4-THIADIAZOLIN-3-CARBOXYLIC ACID ESTERS AND HERBICIDES CONTAINING THE SAME

[75] Inventors: Ludwig Nüsslein; Friedrich Arndt, both of Berlin, Fed. Rep. of Germany

[73] Assignee: Schering Aktiengesellschaft, Berlin and Bergkamen, Fed. Rep. of Germany

[21] Appl. No.: 795,642

[22] Filed: May 10, 1977

[30] Foreign Application Priority Data

May 13, 1976 [DE] Fed. Rep. of Germany ....... 2621647

[51] Int. Cl.$^2$ ...................... A01N 9/12; C07D 285/12
[52] U.S. Cl. ........................................... 71/90; 548/140
[58] Field of Search ..................... 260/306.8 D; 71/90

[56] References Cited

U.S. PATENT DOCUMENTS

| | | | |
|---|---|---|---|
| 3,522,267 | 7/1970 | Duerr et al. | 260/306.8 D |
| 3,840,551 | 10/1974 | Sasse et al. | 260/306.8 D |

*Primary Examiner*—Alton D. Rollins
*Attorney, Agent, or Firm*—Michael J. Striker

[57] ABSTRACT

2-(Dimethylcarbamoylimino)-1,3,4-thiadiazolin-3-carboxylic acid esters of the formula:

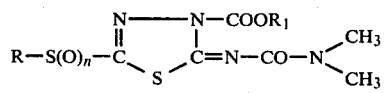

in which R and $R_1$ are aliphatic hydrocarbon groups which may be halogenated, and n is 0, 1 or 2, are effective herbicides, and exhibit a high degree of selectivity toward cultivated plants.

82 Claims, No Drawings

2-(DIMETHYLCARBAMOYLIMINO)-1,3,4-THIADIAZOLIN-3-CARBOXYLIC ACID ESTERS AND HERBICIDES CONTAINING THE SAME

BACKGROUND OF THE INVENTION

Among the known herbicides there are included 1-(1,3,4-thiadiazol-2-yl)-urea derivatives, which are disclosed in Germans DT-PS Nos. 1,816,696 and 2,118,520. However, these herbicides exhibit only a very limited selectivity spectrum toward cultivated plants.

The object of the present invention is therefore the provision of herbicidal agents which will exhibit excellent activity against weeds, and at the same time a broad selectivity spectrum toward cultivated plants.

GENERAL DESCRIPTION OF THE INVENTION

The present invention concerns novel 2-(dimethylcarbamoyl-imino)-1,3,4-thiadiazolin-3-carboxylic acid esters, methods for their preparation, and herbicidal compositions containing these compounds.

The objects are achieved, in accordance with the invention, by a novel herbicidal agent which is broadly a compound of the formula:

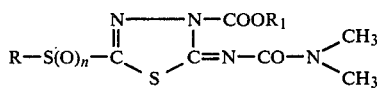

in which R and $R_1$ are aliphatic hydrocarbon groups which can, if desired, be halogenated, and n is 0, 1 or 2.

The compounds of the invention are characterized by a broad herbicidal activity against per-emerged portions of leaves of weeds. They can be applied to the destruction of mono- and dicotylodenous weeds.

By their use, weeds occurring in fields in cultivation, both in pre-emergence and post-emergence stages may be destroyed, such weeds including *Sinapis ssp., stellaria media, Senecio vulgaris, Matricaria chamomilla, Ipomoea purpurea, Chrysanthemum segetum, Lamium amplexicaule, Centaurea cyanus, Amaranthus retroflexus, Alopecurus myosuroides, Echinchloa crus galli, Setaria italica, Sorghum halepense, Lolium perenne*, and many others.

For the control of seminal weeds there are applied amounts ranging from about 1 kg per hectare to about 5 kg per hectare of active agent. In this way there is achieved the aforementioned selective activity toward useful plants, such as potatoes, corn, peanuts, soybeans, peas and other legumes, wheat, barley, sorghum (seed) as well as copse, ornamental shrubbery, and nursery crops.

In larger applications, the compounds of the invention are suitable as complete herbicides for the destruction or suppression of desert plants during a vegetation period.

The agents of the invention can be applied either alone or in admixture with one or more other agents. If desired other plant protecting or pesticidal agents, such as, for example, fungicides, nematocides, and similar agents, depending upon the objective desired, can be added. The addition of fertilizers is also possible.

From the standpoint of broadening the action spectrum, other herbicides can also be added. For example, herbicides which are suitable as active partners include triazines, aminotriazoles, anilides, diazines, uracils, aliphatic carboxylic acids and halogenated carboxylic acids, halogenated benzoic acids, and the hydrazides, amides, nitriles, and esters of these acids, carbamide and thiocarbamide acid esters, ureas, 3,2,6-trichlorobenzyloxypropanol, agents containing thiocyanate groups, and the like. There may also be added other materials, such as non-phytotoxic additives which may provide a synergistic action with the herbicides, including wetting agents, emulsifiers, solvents and oils.

The agents of the invention or their admixtures may be applied in the form of preparations, such as powders, dusts, granules, solutions, emulsions or suspensions, with addition of liquid and/or solid carriers or diluents, and if desired in connection with wetting agents, adhesives, emulsifiers and/or dispersing agents.

Especially suitable as liquid carriers are water, aliphatic and aromatic hydrocarbons, such as benzene, toluene, xylene, cyclohexanone, isophorone, dimethyl sulfoxide, dimethyl formamide, and mineral oil fractions.

As solid carriers there are suitable, mineral earths, such as tonsil, silica gel, talc, kaolin, attaclay, limestone, silica acid, and vegetable products such as flour.

As surface-active agents there can be employed, for example, calcium ligninsulfonate, polyoxyethylenealkylphenyl ethers, naphthalenesulfonic acids and their salts, phenolsulfonic acids and their salts, formaldehyde condensates, fatty alcohol sulfates, and benzenesulfonic acids and their salts.

The content of the active herbicides of the invention in the foregoing preparations can vary over a wide range. For example, the herbicidal preparations contain from about 10% to about 80% by weight of active ingredient, and from about 90% to about 20% by weight of liquid or solid carrier, as well as, if desired, up to 20% by weight of a surface-active agent.

The application of the herbicides can be made in conventional ways, for example as a spray with water as the carrier, in amounts from about 100 to about 1000 liters per hectare. The products may be used in so-called "low volume" and "ultra-low-volume" processes, as well as in the form of so-called microgranules.

Compounds according to the invention which exhibit an especially favorable activity are those having the aforementioned general formula, wherein R is an alkyl, alkenyl or alkinyl group, each having 1 to 6 carbon atoms; $R_1$ is a halogenated alkyl, alkenyl or alkinyl group, each having 1 to 6 carbon atoms; and n signifies the numerals 0, 1 or 2.

Examples of the alkyl, alkenyl and alkinyl groups as defined for R include: methyl, ethyl, propyl, isopropyl, allyl, 2-propinyl, butyl, isobutyl, sec.-butyl, tert,-butyl, 2-butenyl, 2-methyl-2-propenyl, n-pentyl, isopentyl, neopentyl, tert.-pentyl, 1-methylbutyl, 1-ethylpropyl, hexyl, isohexyl and the like.

As examples of $R_1$ there are included: methyl, ethyl, 2,2,2-trichloroethyl, propyl, isopropyl, allyl, 2-propinyl, 3-chloropropyl, n-butyl, isobutyl, sec.-butyl, 2-butenyl, tert.-butyl, pentyl, isopentyl, n-hexyl, and the like.

The novel compounds of the invention can be advantageously prepared, for example, by (a) reacting metal compounds of the general formula:

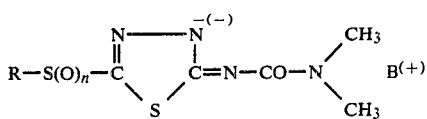

with haloformic acid esters of the general formula;

Hal—CO—O—R₁ or (b) by reacting compounds of the general formula:

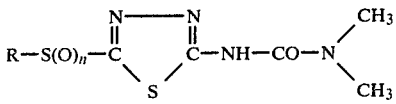

with a haloformic acid ester of the general formula:

Hal—CO—O—R₁

In the presence of an acid-binding agent; or (c) by treating a compound of the general formula:

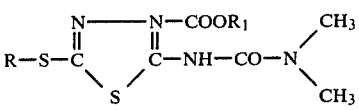

with an oxidizing agent.

In these foregoing reactions, R, R₁ and n have the meaning given above, Hal is a halogen atom, such as chlorine or bromine, and B is a monovalent metal equivalent, for example, lithium, sodium, potassium cations.

The reactions are performed at temperatures in the range of 0° to 120° C., but generally at room temperature. For the synthesis of the compounds of the invention, the reactants are used in approximately equimolecular amounts. As reaction media there are suited polar organic solvents, alone or in admixture with water. Their choice depends upon the metal compounds or the acid binding agents used. As solvents or suspensions media there may be employed acid amides such as dimethylformamide, acid nitriles such as acetonitrile, ethers such as dioxan, ketones such as acetone, and many others.

As acid binding agents there can be employed the usual agents for this purpose. For this purpose there are suited organic bases such as tertiary amines, for example triethylamine or N,N-dimethylaniline, pyridine bases or suitable inorganic bases such as oxides, hydroxides, carbonates, and alkanoic acid salts of the alkali or alkaline earth metals, such as those of sodium, potassium and calcium.

Bases such as pyridine can serve simultaneously as solvents.

As oxidizing agents there may be employed suitable inorganic or organic substances. For the preparation of the compounds of the present invention, when n = 1, the oxidizing agents can be organic hydroperoxides, such as, for example, tert.-butyl hydroperoxide or per-acids, such as, for example, m-chloroperbenzoic acid, or N-halogenic acid amides, such as, for example, N-bromosuccinimide, or inorganic compounds such as, for example, hydrogen peroxide, sodium periodate and the like.

There are added two oxidation equivalents of the oxidizing agent or a small excess, to 1 mol of the thio-compound at temperatures between about 0° and about 60° C.

For the preparation of the compounds of the invention where n is 2, there can be employed besides the oxidizing agents already mentioned, inorganic agents such as potassium permanganate or chromic acid and their salts, or nitric acid or halogens, within a temperature range of about 0° to about 120° C. For 1 mol of thio-compound there are employed analogously, 4 oxidation equivalents or an excess, but at least double the amount with the above described sulfo-oxidation where n is 1.

There may be employed for this purpose, as oxidation media, organic solvents, such as carboxylic acids, for example acetic or formic acid, ethers, for example dioxan, ketones such as acetone, acid amides such as dimethylformamide, carboxylic acid nitriles, such as acetonitrile, or other solvents which are inert toward the above-named oxidizing agents, and these alone or in admixture with water.

The isolation of the produced compounds of the invention takes place either by distilling off the solvent or by precipitation with water.

The starting materials for the preparation of the novel compounds of the invention are generally known compounds.

Those metal compounds not heretofore described in the literature, can be prepared, for example, (a) by reacting dimethylcarbamoyl chloride of the formula:

with 1,3,4-thiadiazolylamides of the formula:

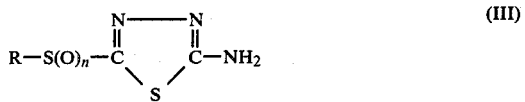

in presence of acid binding agents, to form 2-(dimethylcarbamoylimino)-1,3,4-thiadiazolin-3-carboxylic acid dimethylamino derivatives of the general formula:

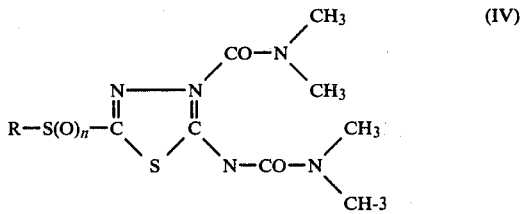

and then reacting this with a metal compound of the formula:

BY        (V)

(b) or by reacting a 1-(1,3,4-thiadiazolyl-2-yl)-3,3-dimethylurea derivative of the general formula:

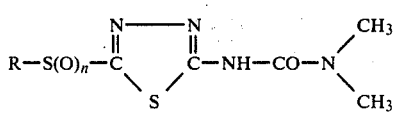

(VI)

with a metal compound of the general formula:

BY  (V)

if necessary with use of a solvent, wherein R, B and n have the aforesaid meanings, and Y is hydrogen, hydroxy, lower alkoxy or amino.

For the synthesis of the compounds according to the invention the reactants are brought together in approximately equimolar amounts. As reaction media there may be used polar organic liquids, alone or in admixture with water. The choice depends upon the type of metal compound BY which is employed. As solvents or suspension media there may be employed acid amides such as dimethylformamide, acid nitriles such as acetonitrile, alcohols such as methanol or ethanol, ethers such as tetrahydrofuran, and the like.

DESCRIPTION OF THE PREFERRED EMBODIMENTS

The following examples serve to illustrate the practice of the invention, but are not to be regarded as limiting.

EXAMPLE 1

80.5 g of 2-(dimethylcarbamoylimino)-5-methylthio-1,3,4-thiadiazol-3-id, sodium salt, were suspended in 300 ml of acetonitrile and treated dropwise with stirring with 36.5 g of ethyl chloroformate at room temperature. The mixture was further stirred for 2 hours, treated with ice water, the precipitated substance separated by suction filtration, and recrystallized from acetonitrile. There is obtained 84.5 g (86.9% of theory) of 2-(dimethylcarbamoylimino)-5-methylthio-1,3,4-thiadiazolin-3-carboxylic acid ethyl ester of m. pt. 129° C.

Analysis: Calculated: C 37.23%; H 4.86%; N 19.30%. Found: C 37.27%; H 4.87%; N 19.16%.

EXAMPLE 2

To a solution of 10.9 g of 1,1-dimethyl-3-(5-methylthio-1,3,4-thiadiazol-2-yl)-urea in 50 ml pyridine there were added dropwise with stirring 11 g of methyl chloroformate, whereupon the temperature of the reaction mixture rose to 50° C. After further stirring for one-half hour the reaction product is precipitated by addition of 300 ml water, filtered by suction, washed with water, and recrystallized from ethanol.

Yield: 11.5 g (83.4% of theory) of 2-(dimethylcarbamoylimino)-5-methylthio-1,3,4-thiadiazolin-3-carboxylic acid methyl ester.

M. pt. 142° C.

Analysis: Calculated: C 34.77%; H 4.38%. Found: C 35.12%; H 4.90%.

EXAMPLE 3

33.2 g of 2(dimethylcarbamoylimino)-5-propylthio-1,3,4-thiadiazolin-3-carboxylic acid isopropyl ester were dissolved in 100 ml glacial acetic acid and 40 ml water. To this solution there is added, at 40° C., 22 g of potassium permangamate, in portions, followed by stirring for 30 minutes and final reduction of the mixture, cooled to 50° C., of precipitated manganese dioxide, by dropwise addition of a solution of 20 g sodium metabisulfite in 200 ml water.

The precipitated substance is precipitated by addition of 500 ml ice water, filtered by suction, washed with water and recrystallized from ethanol. Yield: 30.0 g (82.5% of theory) of 2-(dimethylcarbamoylimino)-5-propylsulfonyl-1,3,4-thiadiazolin-3-carboxylic acid isopropyl ester.

M. pt. 127° C.

Analysis: Calculated: C 39.55%; H 5.53%; N 15.37%. Found: C 39.43%; H 5.76%; N 15.35%.

In analogous manner, the compounds shown in Table 1 may be prepared, in accordance with the invention:

Table 1

| Name | Physical | Constants |
|---|---|---|
| 2-(Dimethylcarbamoylimino)-5-methylsulfonyl-1,3,4-thiadiazolin-3-carboxylic acid-methylester | M. pt. | 178° C. |
| 5-Ethylthio-2-(dimethylcarbamoylimino)-1,3,4-thiadiazolin-3-carboxylic acid-methylester | M. pt. | 126° C. |
| 5-Ethylsulfonyl-2-(dimethylcarbamoylimino)-1,3,4-thiadiazolin-3-carboxylic acid-methylester | M. pt. | 144° C. |
| 2-(Dimethylcarbamoylimino)-5-propylthio, 1,3,4-thiadiazolin-3-carboxylic acid-methylester | M. pt. | 79° C. |
| 5-Ethylthio-2-(dimethylcarbamoylimino)-1,3,4-thiadiazolin-3-carboxylic acid-ethylester | M. pt. | 89° C. |
| 5-Ethylsulfonyl-2-(dimethylcarbamoylimino)-1,3,4-thiadiazolin-3-carboxylic acid-ethylester | M. pt. | 130° C. |
| 2-(Dimethylcarbamoylimino)-5-methylsulfonyl-1,3,4-thiadiazolin-3-carboxylic acid-ethylester | M. pt. | 149° C. |
| 2-(Dimethylcarbamoylimino)-5-propylthio, 1,3,4-thiadiazolin-3-carboxylic acid-isopropylester | M. pt. | 67° C. |
| 2-(Dimethylcarbamoylimino)-5-propylthio-1,3,4-thiadiazolin-3-carboxylic acid-pentylester | M. pt. | 68° C. |
| 2-(Dimethylcarbamoylimino)-5-propylsulfonyl-1,3,4-thiadiazolin-3-carboxylic acid-pentylester | M. pt. | 106° C. |
| 2-Dimethylcarbamoylimino)-5-propylthio-1,3,4-thiadiazolin-3-carboxylic acid-(3-chlorpropyl)-ester | M. pt. | 77° C. |
| 2-(Dimethylcarbamoylimino)-5-methylthio-1,3,4-thiadiazolin-3-carboxylic acid-isopropylester | M. pt. | 97° C. |
| 5-Ethylthio-2-(dimethylcarbamoylimino)-1,3,4-thiadiazolin-3 carboxylic acid-isopropylester | M. pt. | 87° C. |
| 2-(Dimethylcarbamoylimino)-5-methyl thio-1,3,4-thiadiazolin-3-carboxylic acid-isobutylester | M. pt. | 92° C. |
| 2-(Dimethylcarbamoylimino)-5-methylsulfonyl-1,3,4-thiadiazolin-3-carboxylic acid-isobutylester | M. pt. | 125° C. |
| 2-(Dimethylcarbamoylimino)-5-methylsulfonyl-1,3,4-thiadiazolin-3-carboxylic acid-isopropylester | M. pt. | 135° C. |
| 5-Ethylsulfonyl-2-(dimethylcarbamoylimino)-1,3,4-thiadiazolin-3-carboxylic acid-isopropylester | M. pt. | 133° C. |
| 5-Ethylthio-2-(dimethylcarbamoylimino)-1,3,4-thiadiazolin-3-carboxylic acid-pentylester | M. pt. | 70° C. |
| 2-(Dimethylcarbamoylimino)-5-(2-propenylthio)-1,3,4-thiadiazolin-3-carboxylic acid-methylester | M. pt. | 72° C. |
| 2-(Dimethylcarbamoylimino)-5-isopropylthio-1,3,4-thiadiazolin-3-carboxylic acid-(2-propenyl)-ester | M. pt. | 64° C. |
| 2-(Dimethylcarbamoylimino)-5-methylthio-1,3,4-thiadiazolin-3-carboxylic acid-butylester | M. pt. | 125° C. |
| 2-(Dimethylcarbamoylimino)-5-methyl- | | |

Table 1-continued

| Name | Physical | Constants |
|------|----------|-----------|
| thio-1,3,4-thiadiazolin-3-carboxylic acid-(2-propenyl)-ester | M. pt. | 101° C. |
| 2-(Dimethylcarbamoylimino)-5-isopropylthio-1,3,4-thiadiazolin-3-carboxylic acid-butylester | M. pt. | 54° C. |
| 2-(Dimethylcarbamoylimino)-5-methylsulfonyl-1,3,4-thiadiazolin-3-carboxylic acid-butylester | M. pt. | 137° C. |
| 2-(Dimethylcarbamoylimino)-5-methylthio-1,3,4-thiadiazolin-3-carboxylic acid-pentylester | M. pt. | 97° C. |
| 2-(Dimethylcarbamoylimino)-5-isopropylsulfonyl-1,3,4-thiadiazolin-3-carboxylic acid-butylester | M. pt. | 104° C. |
| 2-(Dimethylcarbamoylimino)-5-methylsulfonyl-1,3,4-thiadiazolin-3-carboxylic acid-(2-propenyl)-ester | M. pt. | 113° C. |
| 2-(Dimethylcarbamoylimino)-5-isopropylsulfonyl-1,3,4-thiadiazolin-3-carboxylic acid-(2-propenyl)-ester | M. pt. | 125° C. |
| 2-(Dimethylcarbamoylimino)-5-methylsulfonyl-1,3,4-thiadiazolin-3-carboxylic acid-pentylester | M. pt. | 106° C. |
| 2-(Dimethylcarbamoylimino)-5-isopropylthio-1,3,4-thiadiazolin-3-carboxylic acid-pentylester | M. pt. | 63° C. |
| 2-(Dimethylcarbamoylimino)-5-isobutylthio-1,3,4-thiadiazolin-3-carboxylic acid-(2-propenyl)-ester | M. pt. | 55° C. |
| 2-(Dimethylcarbamoylimino)-5-isobutylthio-1,3,4-thiadiazolin-3-carboxylic acid-butylester | M. pt. | 51° C. |
| 2-(Dimethylcarbamoylimino)-5-pentylthio-1,3,4-thiadiazolin-3-carboxylic acid-methylester | M. pt. | 101° C. |
| 2-(Dimethylcarbamoylimino)-5-hexylsulfinyl-1,3,4-thiadiazolin-3-carboxylic acid-butylester | M. pt. | 83° C. |
| 2-(Dimethylcarbamoylimino)-5-(2-propenylthio)-1,3,4-thiadiazolin-3-carboxylic acid-butylester | M. pt. | 59° C. |
| 2-(Dimethylcarbamoylimino)-5-(2-butenylthio)-1,3,4-thiadiazolin-3-carboxylic acid-butylester | M. pt. | 58° C. |
| 2-(Dimethylcarbamoylimino)-5-(2-butenylthio)-1,3,4-thiadiazolin-3-carboxylic acid-methylester | M. pt. | 96° C. |
| 2-(Dimethylcarbamoylimino)-5-(2-butenylthio)-1,3,4-thiadiazolin-3-carboxylic acid-(2-propenyl)-ester | M. pt. | 59° C. |
| 2-(Dimethylcarbamoylimino)-5-hexylthio-1,3,4-thiadiazolin-3-carboxylic acid-methylester | M. pt. | 86° C. |
| 2-(Dimethylcarbamoylimino)-5-hexylthio-1,3,4-thiadiazolin-3-carboxylic acid-ethylester | M. pt. | 62° C. |
| 2-(Dimethylcarbamoylimino)-5-hexylthio-1,3,4-thiadiazolin-3-carboxylic acid-isopropylester | M. pt. | 56° C. |
| 2-(Dimethylcarbamoylimino)-5-hexylthio-1,3,4-thiadiazolin-3-carboxylic acid-propylester | M. pt. | 55° C. |
| 2-(Dimethylcarbamoylimino)-5-hexylthio-1,3,4-thiadiazolin-3-carboxylic acid-isobutylester | M. pt. | 60° C. |
| 2-(Dimethylcarbamoylimino)-5-hexylthio-1,3,4-thiadiazolin-3-carboxylic acid-butylester | M. pt. | 70° C. |
| 2-(Dimethylcarbamoylimino)-5-isopropylsulfonyl-1,3,4-thiadiazolin-3-carboxylic acid-pentylester | M. pt. | 91° C. |
| 2-(Dimethylcarbamoylimino)-5-isobutylsulfonyl-1,3,4-thiadiazolin-3-carboxylic acid-butylester | M. pt. | 64° C. |
| 2-(Dimethylcarbamoylimino)-5-isobutylsulfonyl-1,3,4-thiadiazolin-5-carboxylic acid(2-propenyl)-ester | M. pt. | 94° C. |
| 2-(Dimethylcarbamoylimino)-5-hexylsulfonyl-1,3,4-thiadiazolin-3-carboxylic acid-ethylester | M. pt. | 74° C. |
| 2-(Dimethylcarbamoylimino)-5-hexylsulfonyl-1,3,4-thiadiazolin-3-carboxylic acid-isopropylester | M. pt. | 70° C. |
| 2-(Dimethylcarbamoylimino)-5-hexylsulfonyl-1,3,4-thiadiazolin-3-carboxylic acid-isobutylester | M. pt. | 91° C. |
| 2-(Dimethylcarbamoylimino)-5-isobutylthio-1,3,4-thiadiazolin-3-carboxylic acid-(2-propinyl)-ester | M. pt. | 103° C. |
| 5-Ethylthio-2-(dimethylcarbamoylimino)-1,3,4-thiadiazolin-3-carboxylic acid-(2-propinyl)-ester | M. pt. | 111° C. |
| 5-Ethylsulfonyl-2-dimethylcarbamoylimino-1,3,4-thiadiazolin-3 carboxylic acid-benzylester | M. pt. | 117° C. |
| 5-Butylsulfonyl-2-(dimethylcarbamoylimino)-1,3,4-thiadiazolin-3 carboxylic acid-butylester | M. pt. | 74° C. |
| 2-(Dimethylcarbamoylimino)-5-(2-propinylthio)-1,3,4-thiadiazolin-3 carboxylic acid-methylester | M. pt. | 101° C. |
| 2-(Dimethylcarbamoylimino)-5-pentylthio-1,3,4-thiadiazolin-3-carboxylic acid-benzylester | M. pt. | 82° C. |
| 2-(Dimethylcarbamoylimino)-5-isobutylsulfonyl-1,3,4-thiadiazolin-3-carboxylic acid-(2-propinyl)-ester | M. pt. | 146° C. |
| 5-Ethylsulfonyl-2-(dimethylcarbamoylimino)-1,3,4-thiadiazolin-3-carboxylic acid-(2-propinyl)-ester | M. pt. | 156° C. |
| 2-(Dimethylcarbamoylimino)-5-pentylsulfonyl-1,3,4-thiadiazolin-3-carboxylic acid-(2-propinyl)-ester | M. pt. | 148° C. |
| 2-(Dimethylcarbamoylimino)-5-pentylthio-1,3,4-thiadiazolin-3-carboxylic acid-butylester | M. pt. | 48° C. |
| 2-(Dimethylcarbamoylimino)-5-(2-methyl-2-propenylthio)-1,3,4-thiadiazolin-3-carboxylic acid-ethylester | M. pt. | 65° C. |
| 2-(Dimethylcarbamoylimino)-5-(2-methyl-2-propenylthio)-1,3,4-thiadiazolin-3-carboxylic acid-propylester | M. pt. | 54° C. |
| 2-(Dimethylcarbamoylimino)-5-(2-methyl-2-propenylthio)-1,3,4-thiadiazolin-3-carboxylic acid-butylester | M. pt. | 47° C. |
| 2-(Dimethylcarbamoylimino)-5-methylthio-1,3,4-thiadiazolin-3-carboxylic acid-(2-propenyl)-ester | M. pt. | 145° C. |
| 2-(Dimethylcarbamoylimino)-5-(2-methyl-2-propenylsulfonyl)-1,3,4-thiadiazolin-3-carboxylic acid-ethylester | M. pt. | 126° C. |
| 2-(Dimethylcarbamoylimino)-5-methylsulfonyl-1,3,4-thiadiazolin-3-carboxylic acid-(2-propinyl)-ester | M. pt. | 155° C. |
| 2-(Dimethylcarbamoylimino)-5-methylthio-1,3,4-thiadiazolin-3-carboxylic acid-2,2,2-trichlor-ethylester | M. pt. | 120° C. |
| 2(Dimethylcarbamoylimino)-5-ethylthio-1,3,4-thiadiazolin-3-carboxylic acid-benzylester | M. pt. | 89° C. |
| 2-(Dimethylcarbamoylimino)-5-isopropylthio-1,3,4-thiadiazolin-3-carboxylic acid-(2-propinyl)-ester | M. pt. | 117° C. |
| 2-(Dimethylcarbamoylimino)-5-butylthio-1,3,4-thiadiazolin-3-carboxylic acid-butylester | M. pt. | 61° C. |
| 2-(Dimethylcarbamoylimino)-5-butylthio-1,3,4-thiadiazolin-3-carboxylic acid-(2-propenyl)-ester | M. pt. | 43° C. |
| 2-(Dimethylcarbamoylimino)-5-butylsulfonyl-1,3,4-thiadiazolin-3-carboxylic acid-(2-propenyl)-ester | M. pt. | 96° C. |
| 2-(Dimethylcarbamoylimino)-5-hexylsulfonyl-1,3,4-thiadiazolin-3-carboxylic acid-butylester | M. pt. | 80° C. |

Table 1-continued

| Name | Physical | Constants |
|---|---|---|
| 2-(Dimethylcarbamoylimino)-5-hexylsulfonyl-1,3,5-thiadiazolin-3-carboxylic acid-propylester | M. pt. | 66° C. |
| 2-(Dimethylcarbamoylimino)-5-methylthio-1,3,4-thiadiazolin-3-carboxylic acid-phenylester | M. pt. | 142° C. |
| 2-(Dimethylcarbamoylimino)-5-methylthio-1,3,4-thiadiazolin-3-carboxylic acid-hexylester | M. pt. | 94° C. |
| 2-(Dimethylcarbamoylimino)-5-methylsulfonyl-1,3,4-thiadiazolin-3-carboxylic acid-hexylester | M. pt. | 101° C. |
| 2-(Dimethylcarbamoylimino)-5-(2-methyl-2-propenylthio)-1,3,4-thiadiazolin-3-carboxylic acid-methylester | M. pt. | 91° C. |

The compounds according to the invention form colorless and odorless crystalline substances, which are slightly soluble in water, but which dissolves well in organic solvents such as hydrocarbons, halogenated hydrocarbons, ethers, ketones, alcohols, carboxylic acids, esters, carboxylic acid amides and carboxylic acid nitriles.

In the following Examples there is described the preparation of useful metal compounds from the starting compounds:

EXAMPLE 4

To a suspension of 30.3 g of 5-ethylthio-2-(dimethylcarbamoylimino)-1,3,4-thiadiazolin-3-carboxylic acid dimethylamide (m.pt. 91° C.) in 200 ml methanol there are added dropwise, with stirring, at room temperature, 6.68 g. of 85% potassium hydroxide dissolved in 100 ml methanol. After standing overnight the reaction mixture is dried in vacuo, the residue digested twice with isopropanol and dried in vacuo.

Yield: 25.2 g (93.4% of theory) of 5-ethylthio-2-(dimethylcarbamoylimino)-1,3,4-thiadiazolin-3-id, potassium salt. M. pt. 250° C.

Analysis: Calculated: C 31.09%; H 4.10%; N 20.72%; K 14.46%. Found: C 30.89%; H 4.31%; N 20.43%; K 14.72%.

The following examples serve to illustrate the utility of the compounds according to the invention:

EXAMPLE 5

The compounds set forth in the following tables were applied in the greenhouse in an amount of 5 kg per hectare, suspended in 500 liters of water per hectare, to sugar beets and tomatoes as test plants, by spraying before and after emergence. Three weeks after treatment, the results were rated on a scale according to which 0=no action and 4=destruction of the plant. As can be seen from Table 2, in general, no destruction of the test plants occurred.

Table 2

| Compound of the Invention | Pre-emergence | | Post-emergence | |
|---|---|---|---|---|
| | Sugar Beet | Tomato | Sugar Beet | Tomato |
| 2-(Dimethylcarbamoylimino)-5-methylthio-1,3,4-thiadiazolin-3-carboxylic acid-methyl-ester | 4 | 4 | 4 | 4 |
| 5-Ethylthio-2-(dimethylcarbamoylimino)-1,3,4-thiadiazolin-3-carboxylic acid-methylester | 4 | 4 | 4 | 4 |
| 2-(Dimethylcarbamoylimino)-5-propylthio-1,3,4-thiadiazolin-3-carboxylic acid-methylester | 4 | 4 | 4 | 4 |
| 2-(Dimethylcarbamoylimino)-5-methylthio-1,3,4-thiadiazolin-3-carboxylic acid-ethylester | 4 | 4 | 4 | 4 |
| 5-(Ethylthio-2-dimethylcarbamoylimino)-1,3,4-thiadiazolin-3-carboxylic acid-ethyl-ester | 4 | 4 | 4 | 4 |
| 2-Dimethylcarbamoylimino)-5-methylsulfonyl-1,3,4-thiadiazolin-3-carboxylic acid-methyl-ester | 4 | 4 | 4 | 4 |
| 5-Ethylsulfonyl-2-(dimethyl-carbamoylimino)-1,3,4-thiadiazolin-3-carboxylic acid-methyl-ester | 4 | 4 | 4 | 4 |
| 5-Ethylsulfonyl-2-(dimethyl-carbamoylimino)-1,3,4-thiadiazolin-3-carboxylic acid-ethyl-ester | 4 | 4 | 4 | 4 |
| 2-(Dimethylcarbamoylimino)-5-methylsulfonyl-1,3,4-thiadiazolin-3-carboxylic acid-ethyl-ester | 4 | 4 | 4 | 4 |
| 2-(Dimethylcarbamoylimino)-imino)-5-propylsulfonyl-1,3,4-thiadiazolin-3-carboxylic acid-isopro- | | | | |

Table 2-continued

| Compound of the Invention | Pre-emergence Sugar Beet | Pre-emergence Tomato | Post-emergence Sugar Beet | Post-emergence Tomato |
|---|---|---|---|---|
| pyl-ester | 4 | 4 | 4 | 4 |
| 2-(Dimethylcarbamoyl-imino)-5-propyl-sulfonyl-1,3,4-thia-diazolin-3-carboxylic acid-pentyl-ester | 4 | 4 | 4 | 4 |
| 2-(Dimethylcarbamoyl-imino)-5-propylthio-1,3,4-thiadiazolin-3-carboxylic acid-isopropylester | 4 | 4 | 4 | 4 |
| 2-(Dimethylcarbamoyl-imino)-5-propylthio-1,3,4-thiadiazolin-3-carboxylic acid-pentylester | 4 | 4 | 4 | 4 |
| 2-(Dimethylcarbamoyl-imino)-5-propylthio-1,3,4-thiadiazolin-3-carboxylic acid,(3-chloropropyl)-ester | 4 | 4 | 4 | 4 |
| 2-(Dimethylcarbamoyl-imino)-5-propylthio-1,3,4-thiadiazolin-3-carboxylic acid-isopropylester | 4 | 4 | 4 | 4 |
| 5-Ethylthio-2-(dimethyl-carbamoylimino)-1,3,4-thiadiazolin-3-carboxylic acid-isopropylester | 4 | 4 | 4 | 4 |
| 2-(Dimethylcarbamoyl-imino)-5-methylthio-1,3,4-thiadiazolin-3-carboxylic acid-isobutylester | 4 | 4 | 4 | 4 |
| 2-(Dimethylcarbamoyl-imino)-5-methylsulfonyl-1,3,4-thiadiazolin-3-carboxylic acid-iso-butyl-ester | 4 | 4 | 4 | 4 |
| 2-(Dimethylcarbamoyl-imino-5-methylsulfonyl-1,3,4-thiadiazolin-3-carboxylic acid-isopropyl-ester | 4 | 4 | 4 | 4 |
| 5-Ethylsulfonyl-2-(dimethylcarbamoyl-imino)-1,3,4-thiadiazolin-3-carboxylic acid-isopropyl-ester | 4 | 4 | 4 | 4 |
| 5-Ethylthio-2-(dimethyl-carbamoylimino)-1,3,4-thiadiazolin-3-carboxylic acid-pentyl-ester | 4 | 4 | 4 | 4 |

EXAMPLE 6

The plants listed below were treated before emergence with the named agents in an amount of 1 kg per hectare. The agent for this purpose was applied to the soil as aqueous suspension with 500 liters water per hectare. The results shown are three weeks after treatment, and demonstrate that the compounds of the invention exhibit a higher selectivity than the comparison compounds. The scale used in Table 3, are 0=total destruction to 10=no injury.

Table 3

| Compounds of the Invention | Peanut | Potato | Pea | Corn | Wheat | Barley | Rice | Seed-Sorghum |
|---|---|---|---|---|---|---|---|---|
| 2-(Dimethylcarbamoylimino)-5-methylthio-1,3,4-thiadiazolin-3-carboxylic acid-methylester | 10 | 10 | 8 | 9 | 8 | 8 | 9 | 8 |
| 5-Ethylthio-2-(dimethylcarbamoyl-imino)-1,3,4-thiadiazolin-3-carboxylic acid-methylester | 10 | 10 | 8 | 9 | 8 | 9 | 10 | 9 |
| 2-(Dimethylcarbamoylimino)-5-propylthio-1,3,4-thiadiazolin-3-carboxylic acid-methylester | 10 | 10 | 10 | 10 | 10 | 9 | 10 | 9 |
| 2-(Dimethylcarbamoylimino)-5-methylthio-1,3,4-thiadiazolin-3-carboxylic acid-ethylester | 10 | 10 | 10 | 8 | 9 | 9 | 9 | 8 |
| 5-Aethylthio-2-(dimethylcarbamoylimino)-1,3,4-thiadiazolin-3-carboxylic acid-ethylester | 10 | 10 | 10 | 8 | 8 | 10 | 10 | 8 |

| Compounds of the Invention | Stellaria media | Senecio vulgaris | Matricharia chamomilla | Centaurea cyanus | Amaranthus retroflexus | Chrysanthemum segetum | Impomoea purpurea | Polygonum lapathifolium | Avena fatua | Echinochloa crus galli | Setaria italica | Digitaria sanguinalis | Sorghum halapense | Poa anua | Lamium amplexicaule |
|---|---|---|---|---|---|---|---|---|---|---|---|---|---|---|---|
| 2-(Dimethylcarbamoylimino)-5-methylthio-1,3,4-thiadiazolin-3-carboxylic acid-methylester | 0 | 0 | 0 | 0 | 0 | 0 | 0 | 0 | 0 | 2 | 0 | 0 | 1 | 1 | 0 |
| 5-Ethylthio-2-(dimethylcarbamoylimino)-1,3,4-thiadiazolin-3-carboxylic acid-methylester | 0 | 0 | 0 | 0 | 0 | 0 | 0 | 0 | 0 | 0 | 0 | 0 | 2 | 1 | 0 |
| 2-(Dimethylcarbamoylimino)-5-propylthio-1,3,4-thiadiazolin-3-carboxylic acid-methylester | 0 | 0 | 0 | 0 | 0 | 0 | 0 | 0 | 2 | 2 | 0 | 0 | 4 | 2 | 0 |
| 2-(Dimethylcarbamoylimino)-5-methylthio-1,3,4-thiadiazolin-3-carboxylic acid-ethylester | 0 | 0 | 0 | 0 | 0 | 0 | 0 | 0 | 0 | 1 | 0 | 0 | 2 | 1 | 0 |
| 5-Ethylthio-2-(dimethylcarbamoylimino)-1,3,4-thiadiazolin-3-carboxylic acid-ethylester | 0 | 0 | 0 | 0 | 0 | 0 | 0 | 0 | 0 | 0 | 0 | 0 | 0 | 0 | 0 |

| Compounds of the Invention | Peanut | Potato | Pea | Corn | Wheat | Barley | Rice | Seed-Sorghum |
|---|---|---|---|---|---|---|---|---|
| 2-(Dimethylcarbamoylimino)-5-methylsulfonyl-1,3,4-thiadiazolin-3-carboxylic acid-methylester | 10 | 8 | 9 | 10 | 8 | 9 | 9 | — |
| 5-Ethylsulfonyl-2-(dimethylcarbamoylimino)-1,3,4-thiadiazolin-3-carboxylic | | | | | | | | |

Table 3-continued

| Compounds of the Invention | Stellaria media | Senecio vulargis | Matricharia chamomilla | Cent-aurea cyanus | Amaranthus retroflexus | Chrysan-themum segetum | Impomoea purpurea | Polygonum lapathifolium | Avena fatua | Echiono-chloa crus galli | Setaria italica | Digitaria sanguinalis | Sorghum halapense | Poa anua | Lamium amplexi-caule |
|---|---|---|---|---|---|---|---|---|---|---|---|---|---|---|---|
| acid-methylester 5-Ethylsulfonyl-2-(dimethyl-carbamoylimino)-1,3,4-thia-diazolin-3-carboxylic acid-ethylester | | | 10 | | 10 | | 8 | 10 | | 8 | | 8 | 10 | | 9 |
| 2-(Dimethylcarbamoylimino)-5-methylsulfonyl-1,3,4-thia-diazolin-3-carboxylic acid-ethylester | | | 10 | | 10 | | 9 | 10 | | — | | — | 10 | | 9 |
| 2-(Dimethylcarbamoylimino)-5-propylsulfonyl-1,3,4-thia-diazolin-3-carboxylic acid-isopropyl-ester | | | 10 | | 9 | | 9 | 10 | | 9 | | 9 | 10 | | 9 |
| | | | 10 | | 10 | | — | 8 | | — | | — | — | | — |
| 2-Dimethylcarbamoylimino)-5-methylsulfonyl-1,3,4-thiadiazolin-3-carboxylic acid-methylester | 0 | 0 | 0 | 0 | 0 | 1 | 0 | 0 | 0 | 0 | 0 | 0 | 0 | 1 | 0 |
| 5-Ethylsulfonyl-2-dimethylcarbamoylimino)-1,3,4-thiadiazolin-3-carboxylic acid-methyl-ester | 0 | 0 | 0 | 0 | 0 | 0 | 0 | 0 | 0 | 0 | 0 | 0 | 0 | 0 | 0 |
| 5-Ethylsulfonyl-2-(dimethylcarbamoylimino)-1,3,4-thiadiazolin-3-carboxylic acid-ethyl-ester | 0 | 0 | 0 | 0 | 0 | 0 | 0 | — | 0 | 0 | 0 | 0 | 0 | — | 0 |
| 2-(Dimethylcarbamoyl-imino)-5-methylsulfonyl-1,3,4-thiadiazolin 3-carboxylic acid-ethyl-ester | 0 | 0 | 0 | 0 | 1 | 0 | 0 | 0 | 0 | 0 | 0 | 0 | 0 | 0 | 0 |
| 2-(Dimethylcarbamoyl-imino)-5-propylsulfonyl-1,3,4-thiadiazolin-3-carboxylic acid-iso-propyl-ester | 0 | 0 | 0 | 0 | 0 | 0 | 10 | 0 | 0 | 2 | 0 | 0 | 0 | 0 | 0 |
| | 0 | 0 | 0 | 0 | 0 | 0 | 0 | 1 | 0 | 1 | 0 | 0 | 1 | 1 | 0 |

| Compounds of the Invention | Peanut | Potato | | | Pea | | Corn | | Wheat | | Barley | | Rice | | Seed-Sorghum |
|---|---|---|---|---|---|---|---|---|---|---|---|---|---|---|---|
| 2-(Dimethylcarbamoylimino)-5-propylsulfonyl 1-1,3,4-thia-diazolin-3-carboxylic acid-pentyl-ester | 10 | 10 | | | — | | 8 | | 8 | | — | | 8 | | 8 |
| 2-(Dimethylcarbamoylimino)-5-propylthio-1,3,4-thiadia-zolin-3-carboxylic acid-iso-propylester | 10 | 10 | | | — | | — | | — | | — | | — | | — |

Table 3-continued

| Compounds of the Invention | Stellaria media | Senecio vulgaris | Matricharia chamomilla | Cent- aurea cyanus | Amaranthus retroflexus | Chrysan- themum segetum | Impomoea purpurea | Polygonum lopathifolium | Avena fatua | Echiono- chloa crus galli | Setaria italica | Digitaria Sanguinails | Sorghum halapense | Poa anua | Lamium amplexi- caule |
|---|---|---|---|---|---|---|---|---|---|---|---|---|---|---|---|
| 2-(Dimethylcarbamoylimino)-5-propylthio-1,3,4-thiadiazolin-3-carboxylic acid- pentylester | | | 10 | | 10 | | — | | | — | | — | 8 | | — |
| 2-(Dimethylcarbamoylimino)-5-propylthio-1,3,4-thiadiazolin-3-carboxylic acid-(3-chlorpropyl)-ester | | | 10 | | 10 | | — | 9 | | — | | — | 9 | | 8 |
| 2-(Dimethylcarbamoylimino)-5-methylthio-1,3,4-thiadiazolin-3-carboxylic acid-isopropylester | | | 10 | | 6 | 8 | | 9 | | 8 | | 9 | 10 | | 10 |
| 2-(Dimethylcarbamoyl- imino)-5-propylsulfonyl- 1,3,4-thiadiazolin-3-carboxylic acid- pentyl- ester | 0 | 0 | 0 | 0 | 0 | 1 | — | 4 | 0 | 1 | 1 | 0 | 3 | 2 | 0 |
| 2-(Dimethylcarbamoyl- imino)-5-propylthio-1,3,4-thiadiazolin-3-carboxylic acid-iso-propylester | 0 | 0 | 0 | 0 | 4 | 0 | 0 | 0 | 0 | 0 | 0 | 0 | 2 | 0 | 0 |
| 2-(Dimethylcarbamoyl- imino)-5-propylthio-1,3,4-thiadiazolin-3-carboxylic acid-penty-lester | 0 | 0 | 0 | 0 | 4 | 0 | 0 | 0 | 1 | 1 | 0 | 0 | 4 | 1 | 0 |
| 2-(Dimethylcarbamoyl- imino)-5-propylthio-1,3,4-thiadiazolin-3-carboxylic acid-(3-chlorpropyl)-ester | 0 | 0 | 0 | 0 | 1 | 0 | 0 | 1 | 1 | 2 | 1 | 0 | 0 | 1 | 1 |
| 2-(Dimethylcarbamoyl- imino)-5-methylthio-1,3,4-thiadiazolin-3-carboxylic acid-isopropylester | 0 | 0 | 0 | 0 | 0 | 0 | 0 | 0 | — | 2 | 1 | 1 | — | 2 | 0 |

| Compounds of the Invention | Peanut | Potato | Pea | Corn | Wheat | Barley | Rice | Seed-Sorghum |
|---|---|---|---|---|---|---|---|---|
| 5-Ethylthio-2-(dimethyl- carbamoylimino)-1,3,4-thiadiazolin-3-carboxylic acid-isopropy-lester | 10 | 6 | — | 6 | 6 | 7 | 7 | 7 |
| 2-(Dimethylcarbamoyl- imino)-5-methylthio-1,3,4-thiadia- zolin-3-carboxylic acid-isobutylester | 10 | 10 | 10 | 10 | 9 | 8 | 10 | 10 |

Table 3-continued

| Compounds of the Invention | Stellaria media | Senecio vulgaris | Matricharia chamomilla | Cent. aurea cyanus | Amaranthus retroflexus | Chrysanthemum segetum | Impomoea purpurea | Polygonum lapathifolium | Avena fatua | Echionochloa crus galli | Setaria italica | Digitaria sanguinalis | Sorghum halapense | Poa anua | Lamium amplexicaule |
|---|---|---|---|---|---|---|---|---|---|---|---|---|---|---|---|
| 2-(Dimethylcarbamoylimino)methylsulfonyl-1,3,4-thiadiazolin-3-carboxylic acid-isobutyl-ester | | | 10 | | 8 | | | 8 | | 8 | | 8 | 8 | 7 | 8 |
| 2-(Dimethylcarbamoylimino)-5-methylsulfonyl-1,3,4-thiadiazolin-3-carboxylic acid-isopropyl-ester | | | 10 | | — | | | 9 | | — | | 8 | — | — | 7 |
| 5-Ethylsulfonyl-2-(dimethylcarbamoylimino)-1,3,4-thiadiazolin-3-carboxylic acid-isopropyl-ester | | | 10 | | — | | 6 | 7 | | 6 | | 7 | 7 | 7 | 8 |
| 5-Ethylthio-2-(dimethylcarbamoylimino)-1,3,4-thiadiazolin-3-carboxylic acid-isopropylester | 0 | 0 | 0 | 0 | 0 | 0 | 0 | 0 | 1 | 0 | 0 | 0 | 1 | 0 | 0 |
| 2-(Dimethylcarbamoylimino)-5-methylthio-1,3,4-thiadiazolin-3-carboxylic acid-isobutylester | 0 | 0 | 0 | 0 | 0 | 0 | 0 | 0 | 4 | 3 | 0 | 1 | — | 0 | 0 |
| 2-(Dimethylcarbamoylimino)-5-methylsulfonyl-1,3,4-thiadiazolin-3-carboxylic acid-isobutyl-ester | 0 | 0 | 0 | 0 | 0 | 0 | — | 0 | 2 | 0 | 0 | 0 | 0 | 1 | 0 |
| 2-(Dimethylcarbamoylimino)-5-methylsulfonyl-1,3,4-thiadiazolin-3-carboxylic acid-isopropyl-ester | 0 | 0 | 0 | 0 | 0 | 0 | 0 | 0 | 1 | 0 | 0 | 0 | 0 | 0 | 0 |
| 5-Ethylsulfonyl-2-(Dimethylcarbamoylimino)-1,3,4-thiadiazolin-3-carboxylic acid-isopropyl-ester | 0 | 0 | 0 | 0 | 0 | 0 | — | 0 | 0 | 0 | 0 | 0 | 0 | 0 | 0 |

| Compounds of the Invention | Peanut | Potato | Pea | Corn | Wheat | Barley | Rice | Seed-Sorghum |
|---|---|---|---|---|---|---|---|---|
| 5-Ethylthio-2-(dimethylcarbamoylimino)-1,3,4-thiadiazolin-3-carboxylic acid-pentylester | 10 | 7 | 6 | 9 | 9 | 8 | 8 | 8 |
| Comparison Compound | | | | | | | | |
| 1,3-Dimethyl-1-(5-tert.-butyl-1,3,4-thiadiazol-2-yl)-urea | 3 | 3 | 0 | 2 | 0 | 0 | 7 | 0 |
| 1,3-Dimethyl-1-(5-trifluor-methyl-1,3,4-thiadiazol-2-yl)-urea | 8 | 6 | 0 | 3 | 0 | 0 | 3 | 0 |

Table 3-continued

| Compounds of the Invention | Stellaria media | Senecio vulgaris | Matricharia chamomilla | Cent-aurea cyanus | Amaranthus retroflexus | Chrysan-themum segetum | Impomoea purpurea | Polygonum lopathifolium | Avena fatua | Echiono-chloa crus galli | Setaria italica | Digitaria sanguinalis | Sorghum halapense | Poa anua | Lamium Amplexi-caule |
|---|---|---|---|---|---|---|---|---|---|---|---|---|---|---|---|
| Untreated | 10 | | 10 | | 10 | 10 | 10 | 10 | | 10 | 10 | 10 | 10 | | 10 |
| 5-ethylthio-2-(dimethyl-carbamoylimino)-1,3,4-thiadia-zolin-3-carboxylic acid-pentylester | 0 | 0 | 0 | 0 | 0 | 0 | 0 | 0 | 2 | 1 | 0 | 0 | 2 | 0 | 0 |
| Comparison Compound | | | | | | | | | | | | | | | |
| 1,3-Dimethyl-1-(5-tert.-bhutyl-1,3,4-thiadiazol)-2-yl)-urea | 0 | 0 | 0 | 0 | 0 | 0 | 0 | 0 | 0 | 0 | 0 | 0 | 0 | 0 | 0 |
| 1,3-Dimethyl-1-(5-trifluormethyl-1,3,4-thiadiazol-2-yl)-urea | 0 | 0 | 0 | 0 | 0 | 0 | 0 | 0 | 0 | 0 | 0 | 0 | 0 | 0 | 0 |
| Untreated | 10 | 10 | 10 | 10 | 10 | 10 | 10 | 10 | 10 | 10 | 10 | 10 | 10 | 10 | 10 |

EXAMPLE 7

The plants listed in Table 4 were treated in the greenhouse after emergence with the listed agents in application amounts of 1 kg agent per hectare. The agent was applied for this purpose as a spray of an aqueous suspension in 500 liters water per hectare. Three weeks after treatment the compounds according to the invention exhibited good selectivity in comparison with the known compounds, on a scale on which 0=total destruction to 10=no injury.

Table 4

| Compounds of the Invention | Peanut | Potato | Pea | Corn | Wheat | Barley | Rice | Seed-Sorghum |
|---|---|---|---|---|---|---|---|---|
| 2-(Dimethylcarbamoylimino)-5-methylthio-1,3,4-thiadiazolin-3-carboxylic acid-methylester | 10 | | 8 | 8 | 9 | 10 | 10 | 10 |
| 5-Ethylthio-2-(dimethylcarbamoylimino)-1,3,4-thiadiazolin-3-carboxylic acid-methylester | 10 | 8 | — | 8 | — | 8 | 8 | — |
| 2-(Dimethylcarbamoylimino)-5-propylthio-1,3,4-thiadiazolin-3-carboxylic acid-methylester | 10 | 8 | 10 | 9 | 8 | 8 | 10 | 8 |
| 2-(Dimethylcarbamoylimino)-5-methylthio-1,3,4-thiadiazolin-3-carboxylic acid-ethylester | 10 | 8 | 8 | 8 | 8 | 8 | 10 | 8 |
| 5-Ethylthio-2-(dimethylcarbamoylimino)-1,3,4-thiadiazolin-3-carboxylic acid-ethylester | 10 | 8 | 9 | — | 9 | 8 | 10 | 8 |

| Compounds of the Invention | Stellaria media | Senecio vulgaris | Matricharia chamomilla | Lamium amplexicaule | Centaurea cyanus | Amaranthus retroflexus | Galium aparine | Chrysanthemum segetum | Ipomoea purpurea | Polygonum lapathifolium | Avena fatua | Alopecurus myosuroides | Echinochloa crus galli | Setaria italica | Digitaria sanguinalis | Sorghum halapense | Poa anua |
|---|---|---|---|---|---|---|---|---|---|---|---|---|---|---|---|---|---|
| 2-(Dimethylcarbamoylimino)-5-methylthio-1,3,4-thiadiazolin-3-carboxylic acid-methylester | 0 | 0 | 0 | 0 | 0 | 0 | 0 | 0 | 0 | 0 | 2 | 1 | 0 | 0 | 0 | 0 | 2 |
| 5-Ethylthio-2-(dimethylcarbamoylimino)1,3,4-thiadiazolin-3-carboxylic acid-methylester | 0 | 0 | 0 | 0 | 0 | 0 | 0 | 0 | 0 | 0 | 0 | 0 | 0 | 0 | 0 | 0 | 1 |
| 2-(Dimethylcarbamoylimino)-5-propylthio-1,3,4-thiadiazolin-3-carboxylic acid-methylester | 0 | 0 | 0 | 0 | 0 | 0 | 0 | 0 | 0 | 0 | 1 | 0 | 0 | 0 | 0 | 0 | 1 |
| 2-(Dimethylcarbamoylimino)-5-methylthio-1,3,4-thiadiazolin-3-carboxylic acid-ethylester | 0 | 0 | 0 | 0 | 0 | 0 | 0 | 0 | 0 | 0 | 2 | 2 | 0 | 0 | 0 | 0 | 1 |
| 5-Ethylthio-2-(dimethylcarbamoylimino)-1,3,4-thiadiazolin-3-carboxylic acid-ethylester | 0 | 0 | 0 | 0 | 0 | 0 | 2 | 0 | 0 | 0 | 3 | 2 | 0 | 0 | 0 | 1 | 2 |

Table 4-continued

| Compounds of the Invention | Peanut | Potato | Pea | Corn | Wheat | Barley | Rice | Seed-Sorghum |
|---|---|---|---|---|---|---|---|---|
| 2-(Dimethylcarbamoylimino)-5-methylsulfonyl-1,3,4-thiadiazolin-3-carboxylic acid-methylester | 10 | — | — | 8 | — | — | 8 | — |
| 5-Ethylsulfonyl-2-(dimethylcarbamoylimino)-1,3,4-thiadiazolin-3-carboxylic acid-methyl-ester | 10 | 10 | — | 8 | — | — | 8 | — |
| 5-Ethylsulfonyl-2-(dimethylcarbamoylimino)-1,3,4-thiadiazolin-3-carboxylic acid-ethylester | 10 | 9 | 8 | 9 | 9 | 9 | 9 | 9 |
| 2-(Dimethylcarbamoylimino)-5-methylsulfonyl-1,3,4-thiadiazolin-3-carboxylic acid-ethylester | 10 | 9 | — | 9 | 9 | 9 | 10 | 8 |
| 2-(Dimethylcarbamoylimino)-5-propylsulfonyl-1,3,4-thiadiazolin-3-carboxylic acid-isopropyl-ester | 10 | 10 | 8 | 10 | 10 | 10 | 10 | 8 |

| Compounds of the Invention | Stellaria media | Senecio vulgaris | Matricharia chamomilla | Lamium amplexicaule | Centaurea cyanus | Amaranthus retroflexus | Galium aparine | Chrysanthemum segetum | Ipomoea purpurea | Polygonum lapathiofolium | Avena fatua | Alopecurus myosuroides | Echinochloa crus galli | Setaria italica | Digitaria sanguinalis | Sorghum halapense | Poa anua |
|---|---|---|---|---|---|---|---|---|---|---|---|---|---|---|---|---|---|
| 2-(Dimethylcarbamoylimino)-5-methylsulfonyl-1,3,4-thiadiazolin-3-carboxylic acid-methylester | 0 | 0 | 0 | 0 | 0 | 0 | 1 | 0 | 0 | 0 | 0 | 0 | 0 | 0 | 0 | 0 | 0 |
| 5-Ethylsulfonyl-2-(dimethylcarbamoylimino)-1,3,4-thiadiazolin-3-carboxylic acid-methylester | 0 | 0 | 0 | 0 | 0 | 0 | 0 | 0 | 1 | 0 | 0 | 0 | 0 | 0 | 0 | 0 | 0 |
| 5-Ethylsulfonyl-2-(dimethylcarbamoylimino)-1,3,4-thiadiazolin-3-carboxylic acid-ethylester | 0 | 0 | 0 | 0 | 0 | 0 | 0 | 0 | 0 | 0 | 0 | 1 | 0 | 0 | 0 | 0 | 2 |
| 2-(Dimethylcarbamoylimino)-5-methylsulfonyl-1,3,4-thiadiazolin-3-carboxylic acid-ethylester | 0 | 0 | 0 | 0 | 0 | 0 | 0 | 0 | 0 | 0 | 1 | 1 | 0 | 0 | 0 | 0 | 2 |
| 2-(Dimethylcarbamoylimino)-5-propyl... | | | | | | | | | | | | | | | | | |

Table 4-continued

| Compounds of the Invention | Peanut | Potato | Pea | Corn | Wheat | Barley | Rice | Seed-Sorghum |
|---|---|---|---|---|---|---|---|---|
| sulfonyl-1,3,4-thiadiazolin-3-carboxylic acid-isopropylester | 0 | 0 | 0 | 1 | 1 | 0 | 0 | 2 |
| 2-(Dimethylcarbamoylimino)-5-propylsulfonyl-1,3,4-thiadiazolin-3-carboxylic acid-pentyl-ester | 10 | 10 | — | 10 | 10 | 8 | 8 | 8 |
| 2-(Dimethylcarbamoylimino)-5-propylthio-1,3,4-thiadiazolin-3-carboxylic acid-isopropylester | 10 | 10 | — | 8 | 8 | 8 | 8 | 9 |
| 2-(Dimethylcarbamoylimino)-5-propylthio-1,3,4-thiadiazolin-3-carboxylic acid-pentylester | 10 | 10 | 10 | 10 | 10 | 8 | 8 | 10 |
| 2-(Dimethylcarbamoylimino)-5-propylthio-1,3,4-thiadiazolin-3-carboxylic acid-(3-chlorpropyl)-ester | 10 | 10 | — | 9 | — | — | — | — |
| 2-(Dimethylcarbamoyl-imino)-5-methylthio-1,3,4-thiadiazolin-3-carboxylic acid-isopropylester | 9 | 8 | — | — | — | — | 8 | — |

| Compounds of the Invention | Stellaria media | Senecio vulgaris | Matricharia chamomilla | Lamium amplexicaule | Centaurea cyanus | Amaranthus retroflexus | Galium aparine | Chrysanthemum segetum | Ipomoea purpurea | Polygonum lapathifolium | Avena fatua | Alopecurus myosuroides | Echinochloa crus galli | Setaria italica | Digitaria sanguinalis | Sorghum halapense | Poa anua |
|---|---|---|---|---|---|---|---|---|---|---|---|---|---|---|---|---|---|
| 2-(Dimethylcarbamoyl-imino)-5-propylsulfonyl-1,3,4-thiadiazolin-3-carboxylic acid-pentylester | 0 | 0 | 0 | 0 | 0 | 0 | 0 | 0 | 5 | 0 | 1 | 3 | 0 | 0 | 0 | 1 | — |
| 2-(Dimethylcarbamoyl-imino)-5-propylthio-1,3,4-thiadiazolin-3-carboxylic acid-isopropylester | 0 | 0 | 0 | 0 | 0 | 0 | 0 | 0 | 0 | 0 | 3 | 1 | 0 | 0 | 0 | 5 | 0 |
| 2-(Dimethylcarbamoyl-imino)-5-propylthio-1,3,4-thiadiazolin-3-carboxylic acid-pentylester | 0 | 0 | 0 | 0 | 0 | 0 | 1 | 0 | 0 | 0 | 4 | 2 | 0 | 0 | 0 | 0 | 0 |
| 2-(Dimethylcarbamoyl-imino)-5-propylthio-1,3,4-thiadiazolin-3-carboxylic acid-(3-chlorpropyl)-ester | 0 | 0 | 0 | 1 | 0 | 0 | 0 | 0 | 0 | — | 3 | 3 | 2 | 0 | 1 | 0 | 4 |

Table 4-continued

| Compounds of the Invention | Stellaria media | Senecio vulgaris | Matricharia chamomilla | Lamium amplexicaule | Centaurea cyanus | Amaranthus retroflexus | Galium aparine | Chrysanthemum segetum | Ipomoea purpurea | Corn | Pea | Potato | Peanut | Wheat | Barley | Rice | Seed-Sorghum |
|---|---|---|---|---|---|---|---|---|---|---|---|---|---|---|---|---|---|
| 2-(Dimethylcarbamoylimino)-5-methylthio-1,3,4-thiadiazolin-3-carboxylic acid-isopropyl-ester | 0 | 0 | 0 | 0 | 0 | 0 | 0 | 0 | 0 | 0 | 0 | 0 | — | 0 | 0 | 4 | 1 |
| 5-Ethylthio-2-(dimethylcarbamoylimino)-1,3,4-thiadiazolin-3-carboxylic acid-isopropylester | | | | 9 | | 8 | | | | 6 | | 8 | 9 | | | 7 | |
| 2-(Dimethylcarbamoylimino)-5-methyl-thio-1,3,4-thiadiazolin-3-carboxylic acid-isobutylester | | | | 8 | | | | | | | | | 8 | | | | |
| 2-(Dimethylcarbamoylimino)-5-methyl-sulfonyl-1,3,4-thiadiazolin-3-carboxylic acid-isobutylester | | | | — | | 6 | | | | | | 6 | — | | | | |
| 2-(Dimethylcarbamoylimino)-4-methyl-sulfonyl-1,3,4-thiadiazolin-3-carboxylic acid-isopropylester | | | | | | 8 | | | | | | 8 | 10 | | | | |
| 5-Ethylsulfonyl-2-(dimethylcarbamoylimino)-1,3,4-thiadiazolin-3-carboxylic acid-isopropylester | | | | 9 | | — | | 0 | | | | — | 9 | | | | |

| Compounds of the Invention | Polygonum lapathifolium | Avena fatua | Alopecurus myosuroides | Echinochloa crus galli | Setaria italica | Digitaria sanguinalis | Sorghum halapense | Poa annua |
|---|---|---|---|---|---|---|---|---|
| 5-Ethylthio-2-(dimethylcarbamoylamino)-1,3,4-thiadiazolin-3-carboxylic acid-isopropylester | 0 | 0 | 1 | 1 | 0 | 0 | 1 | 0 |
| 2-(Dimethylcarbamoylimino)-5-methylthio-1,3,4-thiadiazolin-3-carboxylic acid-isobutylester | 0 | 0 | 0 | 0 | 0 | 0 | 0 | 0 |
| 2-(Dimethylcarbamoylimino)-50methylsulfonyl-1,3,4-thiadiazolin-3-carboxylic acid-isobutylester | 0 | 0 | 0 | 0 | 0 | 0 | 0 | 0 |
| 2-(Dimethylcarbamoyl- | 0 | — | 0 | 0 | 0 | 0 | 0 | 0 |

Table 4-continued

| | Peanut | Potato | Pea | Corn | Wheat | Barley | Rice | Seed-Sorghum |
|---|---|---|---|---|---|---|---|---|
| imino)-5-methylsulfonyl-1,3,4-thiadiazolin-3-carboxylic acid-isopropyl-ester | 0 | 0 | 0 | 0 | 0 | 0 | 0 | 1 |
| 5-Ethylsulfonyl-2-dimethyl-carbamoyl-imino)-13,4,-thiadiazolin-3-carboxylic acid-isopropyl-ester | 0 | 0 | — | 0 | 0 | 0 | 0 | 0 |

| | Stell-aria media | Senecio vulgaris | Matricharia chamomilla | Lamium amplexi-caule | Cent-aurea cyanus | Amaran-thus retro-flexus | Galium aparine | Chrysan-themum segetum | gonum Ipomoea purpurea | Poly- lapathio-folium | curus Avena fatua | Alope-myosur-aides | Echinochloa crus galli | Setaria italica | Digitaria sanguinalis | Sorghum halapense | Poa anua |
|---|---|---|---|---|---|---|---|---|---|---|---|---|---|---|---|---|---|
| Compounds of the Invention | | | | | | | | | | | | | | | | | |
| 5-Ethylthio-2-(dimethylcarbamoyl-imino)-1,3,4-thiadiazolin-3-carboxylic acid-pentylester | 0 | 0 | 0 | — | 0 | 9 | 4 | — | 0 | 0 | 0 | 1 | 0 | 0 | 8 | 4 | 1 |
| Comparison Compounds | | | | | | | | | | | | | | | | | |
| 1,3-Dimethyl-1-(5-tert.-butyl-1,3,4-thiadiazol-3-yl)-urea | 0 | 0 | 0 | 6 | 0 | 0 | 0 | 0 | 0 | 0 | 0 | 0 | 0 | 0 | 0 | 0 | 0 |
| 1,3-Dimethyl-1-(5-Trifluor-methyl-1,3,4-thiadiazol-2-yl)-urea | 0 | 0 | 0 | 4 | 0 | 0 | 0 | 0 | 0 | 0 | 3 | 0 | 0 | 0 | 0 | 0 | 0 |
| Untreated | 110 | 10 | 10 | 10 | 10 | 10 | 10 | 10 | 10 | 10 | 10 | 10 | 10 | 10 | 10 | 10 | 10 |

| | Stell-aria media | Senecio vulgaris | Matricharia chamomilla | Lamium amplexi-caule | Cent-aurea cyanus | Amaran-thus retro-flexus | Galium aparine | Chrysan-themum segetum | gonum Ipomoea purpurea | Poly- lapathio-folium | curus Avena fatua | Alope-myosur-aides | Echinochloa crus galli | Setaria italica | Digitaria sanguinalis | Sorghum halapense | Poa anua |
|---|---|---|---|---|---|---|---|---|---|---|---|---|---|---|---|---|---|
| Compounds of the Invention | | | | | | | | | | | | | | | | | |
| 5-Ethylthio-2-(dimethyl-carbamoyl-imino)-1,3,4-thiadiazolin-3-carboxylic acid-pentylester | | | | | | | | | | | | | | | | | |
| Comparison Compounds | | | | | | | | | | | | | | | | | |
| 1,3-Dimethyl-1-(5-tert.-butyl-1,3,4-thiadiazol-2-yl)-urea | | | | | | | | | | | | | | | | | |
| 1,3-Dimethyl-1-(5-tri-fluormethyl-1,3,4-thia-diazol-2-yl)-urea | | | | | | | | | | | | | | | | | |
| Untreated | | | | | | | | | | | | | | | | | |

EXAMPLE 8

The compounds listed in Table 5 were applied in the greenhouse in amounts of 5 kg agent per hectare, suspended in 500 litwer of water per hectare, to *Sinapis sp.* and *Solanum sp.* as test plants by spraying before and after emergence. Three weeks after the treatment the results were measured according to a scale on which 0=no action to 4=destruction of the plant. As can be seen from the table, as a rule, no injury to the test plants resulted.

Table 5

| Compounds of the Invention | Pre-emergence | | Post-emergence | |
|---|---|---|---|---|
| | Sinapis sp. | Solanum sp. | Sinapis sp. | Solanum sp. |
| 2-(Dimethylcarbamoyl-imino)-5-pentylsulfonyl-1,3,4-thiadiazolin-3-carboxylic acid-(2-propinyl)-ester | 4 | 4 | 4 | 4 |
| 2-(Dimethylcarbamoyl-amino)-5-pentylthio-1,3,4-thiadiazolin-3-carboxylic acid-butylester | — | 3 | 4 | 4 |
| 2-(Dimethylcarbamoyl-imino)-5-ethylthio-1,3,4-thiadiazolin-3-carboxylic acid-benzylester | 4 | 4 | 4 | 4 |
| 5-Ethylsulfonyl-2-(dimethyl-carbamoylimino)-1,3,4-thiadiazolin-3-carboxylic acid-benzylester | 4 | 4 | 4 | 4 |
| 5-Butylsulfonyl-2-(dimethyl-carbamoylimino)-1,3,4-thiadiazolin-3-carboxylic acid-butylester | 4 | 4 | 4 | 4 |
| 2-(Dimethylcarbamoylimino)-5-(2-propinylthio)-1,3,4-thiadiazolin-3-carboxylic acid-methylester | — | — | — | — |
| 2(Dimethylcarbamoylimino)-5-pentylthio-1,3,4-thiadiazolin-3-carboxylic acid-benzylester | — | — | 4 | — |
| 2-(Dimethylcarbamoylimino)-5-isobutylsulfonyl-1,3,4-thiadiazolin-3-carboxylic acid-(2-propinyl)-ester | 4 | 4 | 4 | 4 |
| 5-Ethylsulfonyl-2-(dimethyl-carbamoylimino)-1,3,4-thiadiazolin-3-carboxylic acid-(2-propinyl)-ester | 4 | 4 | 4 | 4 |
| 2-(Dimethylcarbamoylimino)-5-(2-methyl-2-propenylsulfonyl)-1,3,4-thiadiazolin-3-carboxylic acid-ethylester | 4 | 4 | 4 | 4 |
| 2-(Dimethylcarbamoylimino)-5-methylsulfonyl-1,3,4-thiadiazolin-3-carboxylic acid-(2-propinyl)-ester | 4 | 4 | 4 | 4 |
| 2-(Dimethylcarbamoylimino)-5-methylthio-1,3,4-thiadiazolin-3-carboxylic acid-2,2,2-trichlor-ethylester | 4 | 4 | 4 | 4 |
| 2-(Dimethylcarbamoylimino)-5-isopropylthio-1,3,4-thiadiazolin-3-carboxylic acid-(2-propinyl)-ester | 4 | 4 | 4 | 4 |
| 2-(Dimethylcarbamoylimino)-5-isobutylthio-1,3,4-thiadiazolin-3-carboxylic acid-(2-propinyl)-ester | 4 | 4 | 4 | 4 |
| 5-Ethylthio-2-(dimethylcarbamoyl-imino)-1,3,4-thiadiazolin-3-carboxylic acid-(2-propinyl)-ester | 4 | 4 | 4 | 4 |
| 2-(Dimethylcarbamoylimino)-5-methylsulfonyl-1,3,4-thiadiazolin-3-carboxylic acid-hexylester | 4 | 4 | 4 | 4 |
| 2-(Dimethylcarbamoylimino)-5-(2-methyl-2-propenylthio)-1,3,4-thiadiazolin-3-carboxylic acid-methylester | 4 | 4 | 4 | 4 |
| 2-(Dimethylcarbamoylimino)-5-(2-methyl-2-propenylthio)-1,3,4-thiadiazolin-3-carboxylic acid-ethylester | 4 | 4 | 4 | 4 |
| 2-(Dimethylcarbamoylimino)-5- | | | | |

Table 5-continued

| Compounds of the Invention | Pre-emergence | | Post-emergence | |
|---|---|---|---|---|
| | Sinapis sp. | Solanum sp. | Sinapis sp. | Solanum sp. |
| (2-methyl-2-propenylthio)-1,3,4-thiadiazolin-3-carboxylic acid-propylester | 4 | 4 | 4 | 4 |
| 2-(Dimethylcarbamoylimino)-5-(2-methyl-2-propenylthio)-1,3,4-thiadiazolin-3-carboxylic acid-butylester | 4 | 4 | 4 | 4 |
| 2-(Dimethylcarbamoylimino)-5-methylthio-1,3,4-thiadiazolin-3-carboxylic acid-(2-propenyl)-ester | 4 | 4 | 4 | 4 |
| 2-(Dimethylcarbamoylimino)-5-butylthio-1,3,4-thiadiazolin-3-carboxylic acid-butylester | 4 | 4 | 4 | 4 |
| 2-(Dimethylcarbamoylimino)-5-butylthio-1,3,4-thiadiazolin-3-carboxylic acid-(2-propenyl)-ester | 3 | — | 4 | 4 |
| 2-(Dimethylcarbamoylimino)-5-butylsulfonyl-1,3,4-thiadiazolin-3-carboxylic acid-(2-propenyl)-ester | 4 | 4 | 4 | 4 |
| 2-(Dimethylcarbamoylimino)-5-hexylsulfonyl-1,3,4-thiadiazolin-3-carboxylic acid-butylester | 4 | 4 | 4 | 4 |
| 2-(Dimethylcarbamoylimino)-5-hexylsulfonyl-1,3,4-thiadiazolin-3-carboxylic acid-propylester | 4 | 4 | 4 | 4 |
| 2-(Dimethylcarbamoylimino)-5-methylthio-1,3,4-thiadiazolin-3-carboxylic acid-phenylester | 4 | 4 | 4 | 4 |
| 2-(Dimethylcarbamoylimino)-5-methylthio-1,3,4-thiadiazolin-3-carboxylic acid-hexylester | 4 | 4 | 4 | 4 |
| 2-(Dimethylcarbamoylimino)-5-hexylsulfonyl-1,3,4-thiadiazolin-3-carboxylic acid-ethylester | — | — | 4 | 4 |
| 2-(Dimethylcarbamoylimino)-5-hexylsulfonyl-1,3,4-thiadiazolin-3-carboxylic acid-ethylester | — | — | 4 | 4 |
| 2-(Dimethylcarbamoylimino)-5-hexylsulfonyl-1,3,4-thiadiazolin-3-carboxylic acid-isopropylester | — | — | 4 | 4 |
| 2-(Dimethylcarbamoylimino)-5-hexylsulfonyl-1,3,4-thiadiazolin-3-carboxylic acid-isobutylester | — | — | 4 | 4 |
| 2-(Dimethylcarbamoylimino)-5-hexylthio-1,3,4-thiadiazolin-3-carboxylic acid-propylester | — | — | 4 | 4 |
| 2-(Dimethylcarbamoylimino)-5-hexylthio-1,3,4-thiadiazolin-3-carboxylic acid-isobutylester | — | — | 4 | 4 |
| 2-(Dimethylcarbamoylimino)-5-hexylthio-1,3,4-thiadiazolin-3-carboxylic acid-butylester | — | — | 4 | 4 |
| 2-(Dimethylcarbamoylimino)-5-isopropylsulfonyl-1,3,4-thiadiazolin-3-carboxylic acid-pentylester | — | — | 4 | 4 |
| 2-(Dimethylcarbamoylimino)-5-isobutylsulfonyl-1,3,4-thiadiazolin-3-carboxylic acid-butylester | — | — | 4 | 4 |
| 2-(Dimethylcarbamoylimino)-5-isobutylsulfonyl-1,3,4-thiadiazolin-5-carboxylic acid-(2-propenyl)-ester | — | — | 4 | 4 |
| 2-(Dimethylcarbamoylimino)-5-(2-butenylthio)-1,3,4-thiadiazolin-3-carboxylic acid-butylester | 4 | 4 | 4 | 4 |
| 2-(Dimethylcarbamoylimino)-5-(2-butenylthio)-1,3,4-thiadiazolin-3-carboxylic acid-methylester | 4 | 4 | 4 | 4 |
| 2-(Dimethylcarbamoylimino)-5- | | | | |

Table 5-continued

| Compounds of the Invention | Pre-emergence | | Post-emergence | |
|---|---|---|---|---|
| | Sinapis sp. | Solanum sp. | Sinapis sp. | Solanum sp. |
| (2-butenylthio)-1,3,4-thiadiazolin-3-carboxylic acid-(2-propenyl)-ester | 4 | 4 | 4 | 4 |
| 2-(Dimethylcarbamoylimino)-5-hexylthio-1,3,4-thiadiazolin-3-carboxylic acid-methylester | — | — | 4 | 4 |
| 2-(Dimethylcarbamoylimino)-5-hexylthio-1,3,4-thiadiazolin-3-carboxylic acid-ethylester | — | — | 4 | 4 |
| 2-(Dimethylcarbamoylimino)-5-hexylthio-1,3,4-thiadiazolin-3-carboxylic acid-isopropyl-ester | — | — | 4 | 4 |
| 2-(Dimethylcarbamoylimino)-5-isopropylthio-1,3,4-thiadiazolin-3-carboxylic acid-pentylester | 4 | 4 | 4 | 4 |
| 2-(Dimethylcarbamoylimino)-5-isobutylthio-1,3,4-thiadiazolin-3-carboxylic acid-(2-propenyl)-ester | 4 | 4 | 4 | 4 |
| 2-(Dimethylcarbamoylimino)-5-isobutylthio-1,3,4-thiadiazolin-3-carboxylic acid-butylester | 4 | 4 | 4 | 4 |
| 2-(Dimethylcarbamoylimino)-5-pentylthio-1,3,4-thiadiazolin-3-carboxylic acid-methylester | — | — | 4 | 4 |
| 2-(Dimethylcarbamoylimino)-5-hexylsulfinyl-1,3,4-thiadiazolin-3-carboxylic acid-butylester | 4 | 4 | 4 | 4 |
| 2-(Dimethylcarbamoylimino)-5-(2-propenylthio)-1,3,4-thiadiazolin-3-carboxylic acid-butylester | 4 | 4 | 4 | 4 |
| 2-(Dimethylcarbamoylimino)-5-methylsulfonyl-1,3,4-thiadiazolin-3-carboxylic acid-butylester | 4 | 4 | 4 | 4 |
| 2-(Dimethylcarbamoylimino)-5-methylthio-1,3,4-thiadiazolin-5-carboxylic acid-pentylester | 4 | 4 | 4 | 4 |
| 2-(Dimethylcarbamoylimino)-5-isopropylsulfonyl-1,3,4-thiadiazolin-3-carboxylic acid-butylester | 4 | 4 | 4 | 4 |
| 2-(Dimethylcarbamoylimino)-5-methylsulfonyl-1,3,4-thiadiazolin-3-carboxylic acid-(2-propenyl)-ester | 4 | 4 | 4 | 4 |
| 2-(Dimethylcarbamoylimino)-5-isopropylsulfonyl-1,3,4-thiadiazolin-3-carboxylic acid-(2-propenyl)-ester | 4 | 4 | 4 | 4 |
| 2-(Dimethylcarbamoylimino)-5-methylsulfonyl-1,3,4-thiadiazolin-3-carboxylic acid-pentylester | 4 | 4 | 4 | 4 |
| 2-(Dimethylcarbamoylimino)-5-(2-propenylthio)-1,3,4-thiadiazolin-3-carboxylic acid-methylester | 4 | 4 | 4 | 4 |
| 2-(Dimethylcarbamoylimino)-5-isopropylthio-1,3,4-thiadiazolin-3-carboxylic acid-(2-propenyl)-ester | 4 | 4 | 4 | 4 |
| 2-(Dimethylcarbamoylimino)-5-methylthio-1,3,4-thiadiazolin-3-carboxylic acid-butylester | 4 | 4 | 4 | 4 |
| 2-(Dimethylcarbamoylimino)-5-methylthio-1,3,4-thiadiazolin-3-carboxylic acid-(2-propenyl)-ester | 4 | 4 | 4 | 4 |
| 2-(Dimethylcarbamoylimino)-5-isopropylthio-1,3,4-thiadiazolin-3-carboxylic acid-(2-propenyl)-ester | — | — | 4 | 4 |
| 2-(Dimethylcarbamoylimino)-5-isopropylthio,1,3,4-thiadia- | | | | |

Table 5-continued

| Compounds of the Invention | Pre-emergence | | Post-emergence | |
|---|---|---|---|---|
| | Sinapis sp. | Solanum sp. | Sinapis sp. | Solanum sp. |
| zolin-3-carboxylic acid-butylester | 4 | 4 | 4 | 4 |

What is claimed is:

1. A 2-(dimethylcarbamoylimino)-1,3,4-thiadiazolin-3-carboxylic acid ester of the formula:

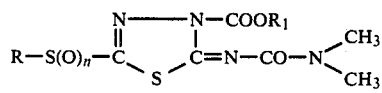

in which R is selected from the group consisting of alkyl of 1 to 6 carbon atoms, 2-alkenyl or 2-alkynyl radicals, each having up to 6 carbon atoms; $R_1$ is selected from the group consisting of
 (a) alkyl having from 1 to 6 carbon atoms,
 (b) 2-alkenyl or 2-alkinyl, each having up to 6 carbon atoms,
 (c) mono and trihalogenated alkyl, 2-alkenyl or 2-alkinyl, each having up to 6 carbon atoms, and
 (d) phenyl or benzyl; and
n is 0, 1, or 2.

2. A compound as defined in claim 1 wherein $R_1$ is selected from the group consisting of 3-chloropropyl and trichloroethyl.

3. A compound according to the formula set forth in claim 1, which is 2-(dimethylcarbamoylimino)-methylthio-1,3,4-thiadiazolin-3-carboxylic acid ethylester.

4. A compound according to the formula set forth in claim 1, which is 2-(dimethylcarbamoylimino)-5-methylthio-1,3,4-thiadiazolin-3-carboxylic acid-methylester.

5. A compound according to the formula set forth in claim 1, which is 2-(dimethylcarbamoylimino)-5-propylsulfonyl-1,3,4-thiadiazolin-3-carboxylic acid-isopropylester.

6. A compound according to the formula set forth in claim 1, which is 2-(dimethylcarbamoylimino)-5-methylsulfonyl-1,3,4-thiadiazolin-3-carboxylic acid-methylester.

7. A compound according to the formula set forth in claim 1, which is 5-ethylthio-2-(dimethylcarbamoylimino)-1,3,4-thiadiazolin-3-carboxylic acid-methylester.

8. A compound according to the formula set forth in claim 1, which is 5-ethylsulfonyl-2-(dimethylcarbamoylimino)-1,3,4-thiadiazolin-3-carboxylic acid-methylester.

9. A compound according to the formula set forth in claim 1, which is 2-(dimethylcarbamoylimino)-5-propylthio-1,3,4-thiadiazolin-3-carboxylic acid-methylester.

10. A compound according to the formula set forth in claim 1, which is 5-ethylthio-2-(dimethylcarbamoylimino)-1,3,4-thiadiazolin-3-carboxylic acid-ethylester.

11. A compound according to the formula set forth in claim 1, which is 5-ethylsulfonyl-2-(dimethylcarbamoylimino)-1,3,4-thiadiazolin-3-carboxylic acid-ethylester.

12. A compound according to the formula set forth in claim 1, which is 2-(dimethylcarbamoylimino)-5-methylsulfonyl-1,3,4-thiadiazolin-3-carboxylic acid-ethylester.

13. A compound according to the formula set forth in claim 1, which is 2-(dimethylcarbamoylimino)-5-propylthio-1,3,4-thiadiazolin-3-carboxylic acid-isopropylester.

14. A compound according to the formula set forth in claim 1, which is 2-(dimethylcarbamoylimino)-5-propylthio-1,3,4-thiadiazolin-3-carboxylic acid-pentylester.

15. A compound according to the formula set forth in claim 1, which is 2-(dimethylcarbamoylimino)-5-propylsulfonyl-1,3,4-thiadiazolin-3-carboxylic acid-pentylester.

16. A compound according to the formula set forth in claim 1, which is 2-(dimethylcarbamoylimino-5-propylthio-1,3,4-thiadiazolin-3-carboxylic acid-(3-chloropropyl)-ester.

17. A compound according to the formula set forth in claim 1, which is 2-(dimethylcarbamoylimino)-5-methylthio-1,3,4-thiadiazolin-3-carboxylic acid-isopropylester.

18. A compound according to the formula set forth in claim 1, which is 5-ethylthio-2-(dimethylcarbamoylimino)-1,3,4-thiadiazolin-3-carboxylic acid-isopropylester.

19. A compound according to the formula set forth in claim 1, which is 2-(dimethylcarbamoylimino)-5-methylthio-1,3,4-thiadiazolin-3-carboxylic acid-isobutylester.

20. A compound according to the formula set forth in claim 1, which is 2-(dimethylcarbamoylimino)-5-methylsulfonyl-1,3,4-thiadiazolin-3-carboxylic acid-isobutylester.

21. A compound according to the formula set forth in claim 1, which is 2-dimethylcarbamoylimino)-5-methylsulfonyl-1,3,4-thiadiazolin-3-carboxylic acid-isopropylester.

22. A compound according to the formula set forth in claim 1, which is 5-ethylsulfonyl-2-(dimethylcarbamoylimino)-1,3,4-thiadiazolin-3-carboxylic acid-isopropylester.

23. A compound according to the formula set forth in claim 1, which is 5-ethylthio-2-(dimethylcarbamoylimino)-1,3,4-thiadiazolin-3-carboxylic acid-pentylester.

24. A compound according to the formula set forth in claim 1, which is 2-(dimethylcarbamoylimino)-5-(2-propenylthio)-1,3,4-thiadiazolin-3-carboxylic acid-methylester.

25. A compound according to the formula set forth in claim 1, which is 2-(dimethylcarbamoylimino)-5-isopropylthio-1,3,4-thiadiazolin-3-carboxylic acid-(2-propenyl)-ester.

26. A compound according to the formula set forth in claim 1, which is 2-(dimethylcarbamoylimino)-5-methylthio-1,3,4-thiadiazolin-3-carboxylic acid-butylester.

27. A compound according to the formula set forth in claim 1, which is 2-(dimethylcarbamoylimino)-5-methylthio-1,3,4-thiadiazolin-3-carboxylic acid-(2-propenyl)-ester.

28. A compound according to the formula set forth in claim 1, which is 2-(dimethylcarbamoylimino)-5-isopropylthio-1,3,4-thiadiazolin-3-carboxylic acid-butylester.

29. A compound according to the formula set forth in claim 1, which is 2-(dimethylcarbamoylimino)-5-methylsulfonyl-1,3,4-thiadiazolin-3-carboxylic acid butylester.

30. A compound according to the formula set forth in claim 1, which is 2-(dimethylcarbamoylimino)-5-methylthio-1,3,4-thiadiazolin-3-carboxylic acid-pentylester.

31. A compound according to the formula set forth in claim 1, which is 2-(dimethylcarbamoylimino)-5-isopropylsulfonyl-1,3,4-thiadiazolin-3-carboxylic acid-butylester.

32. A compound according to the formula set forth in claim 1, which is 2-(dimethylcarbamoylimino)-5-methylsulfonyl-1,3,4-thiadiazolin-3-carboxylic acid-(2-propenyl)-ester.

33. A compound according to the formula set forth in claim 1, which is 2-(dimethylcarbamoylimino)-5-isopropylsulfonyl-1,3,4-thiadiazolin-3-carboxylic acid-(2-propenyl)-ester.

34. A compound according to the formula set forth in claim 1, which is 2-(dimethylcarbamoylimino)-5-methylsulfonyl-1,3,4-thiadiazolin-3-carboxylic acid-pentylester.

35. A compound according to the formula set forth in claim 1, which is 2-(dimethylcarbamoylimino)-5-isopropylthio-1,3,4-thiadiazolin-3-carboxylic acid-pentylester.

36. A compound according to the formula set forth in claim 1, which is 2-(dimethylcarbamoylimino)-5-isobutylthio-1,3,4-thiadiazolin-3-carboxylic acid-(2-propenyl)-ester.

37. A compound according to the formula set forth in claim 1, which is 2-(dimethylcarbamoylimino)-5-isobutylthio-1,3,4-thiadiazolin-3-carboxylic acid-butylester.

38. A compound according to the formula set forth in claim 1, which is 2-(dimethylcarbamoylimino)-5-pentylthio-1,3,4-thiadiazolin-3-carboxylic acid-methylester.

39. A compound according to the formula set forth in claim 1, which is 2-(dimethylcarbamoylimino)-5-hexylsulfinyl-1,3,4-thiadiazolin-3-carboxylic acid-butylester.

40. A compound according to the formula set forth in claim 1, which is 2-(dimethylcarbamoylimino)-5-(2-propenylthio)-1,3,4-thiadiazolin-3-carboxylic acid-butylester.

41. A compound according to the formula set forth in claim 1, which is 2-(dimethylcarbamoylimino)-5-(2-butenylthio)-1,3,4-thiadiazolin-3-carboxylic acid-butylester.

42. A compound according to the formula set forth in claim 1, which is 2-(dimethylcarbamoylimino)-5-(2-butenylthio)-1,3,4-thiadiazolin-3-carboxylic acid-methylester.

43. A compound according to the formula set forth in claim 1, which is 2-(dimethylcarbamoylimino)-5-(2-butenylthio)-1,3,4-thiadiazolin-3-carboxylic acid-(2-propenyl)-ester.

44. A compound according to the formula set forth in claim 1, which is 2-(dimethylcarbamoylimino)-5-hexylthio-1,3,4-thiadiazolin-3-carboxylic acid-methylester.

45. A compound according to the formula set forth in claim 1, which is 2-(dimethylcarbamoylimino)-5-hexylthio-1,3,4-thiadiazolin-3-carboxylic acid-ethylester.

46. A compound according to the formula set forth in claim 1, which is 2-(dimethylcarbamoylimino)-5-hexylthio-1,3,4-thiadiazolin-3-carboxylic acid-isopropylester.

47. A compound according to the formula set forth in claim 1, which is 2-(dimethylcarbamoylimino)-5-hexylthio-1,3,4-thiadiazolin-3-carboxylic acid-propylester.

48. A compound according to the formula set forth in claim 1, which is 2-(dimethylcarbamoylimino)-5-hexylthio-1,3,4-thiadiazolin-3-carboxylic acid-butylester.

49. A compound according to the formula set forth in claim 1, which is 2-(dimethylcarbamoylimino)-5-isopropylsulfonyl-1,3,4-thiadiazolin-3-carboxylic acid-pentylester.

50. A compound according to the formula set forth in claim 1, which is 2-(dimethylcarbamoylimino)-5-isobutylsulfonyl-1,3,4-thiadiazolin-3-carboxylic acid-butylester.

51. A compound according to the formula set forth in claim 1, which is 2-(dimethylcarbamoylimino)-5-isobutylsulfonyl-1,3,4-thiadiazolin-5-carboxylic acid-(2-propenyl)-ester.

52. A compound according to the formula set forth in claim 1, which is 2-(dimethylcarbamoylimino)-5-hexylsulfonyl-1,3,4-thiadiazolin-3-carboxylic acid-ethylester.

53. A compound according to the formula set forth in claim 1, which is 2-(dimethylcarbamoylimino)-5-hexylsulfonyl-1,3,4-thiadiazolin-3-carboxylic acid-isopropylester.

54. A compound according to the formula set forth in claim 1, which is 2-(dimethylcarbamoylimino)-5-hexylsulfonyl-1,3,4-thiadiazolin-3-carboxylic acid-isobutylester.

55. A compound according to the formula set forth in claim 1, which is 2-(dimethylcarbamoylimino)-5-butylthio-1,3,4-thiadiazolin-3-carboxylic acid-butylester.

56. A compound according to the formula set forth in claim 1, which is 2-(dimethylcarbamoylimino)-5-butylthio-1,3,4-thiadiazolin-3-carboxylic acid-(2-propenyl)-ester.

57. A compound according to the formula set forth in claim 1, which is 2-(dimethylcarbamoylimino)-5-butylsulfonyl-1,3,4-thiadiazolin-3-carboxylic acid-(2-propenyl)-ester.

58. A compound according to the formula set forth in claim 1, which is 2-(dimethylcarbamoylimino)-5-hexylsulfonyl-1,3,4-thiadiazolin-3-carboxylic acid-butylester.

59. A compound according to the formula set forth in claim 1, which is 2-(dimethylcarbamoylimino)-5-hexylsulfonyl-1,3,4-thiadiazolin-3-carboxylic acid-propylester.

60. A compound according to the formula set forth in claim 1, which is 2-(dimethylcarbamoylimino)-5-methylthio-1,3,4-thiadiazolin-3-carboxylic acid-phenylester.

61. A compound according to the formula set forth in claim 1, which is 2-(dimethylcarbamoylimino)-5-methylthio-1,3,4-thiadiazolin-3-carboxylic acid-hexylester.

62. A compound according to the formula set forth in claim 1, which is 2-(dimethylcarbamoylimino)-5-methylsulfonyl-1,3,4-thiadiazolin-3-carboxylic acid-hexylester.

63. A compound according to the formula set forth in claim 1, which is 2-(dimethylcarbamoylimino)-5-(2-methyl-2-propenylthio)-1,3,4-thiadiazolin-3-carboxylic acid-methylester.

64. A compound according to the formula set forth in claim 1, which is 2-(dimethylcarbamoylimino)-5-(2-methyl-2-propenylthio)-1,3,4-thiadiazolin-3-carboxylic acid-ethylester.

65. A compound according to the formula set forth in claim 1, which is 2-(dimethylcarbamoylimino)-5-(2-methyl-2-propenylthio)-1,3,4-thiadiazolin-3-carboxylic acid-propylester.

66. A compound according to the formula set forth in claim 1, which is 2-(dimethylcarbamoylimino)-5-(2-methyl-2-propenylthio)-1,3,4-thiadiazolin-3-carboxylic acid-butylester.

67. A compound according to the formula set forth in claim 1, which is 2-(dimethylcarbamoylimino)-5-(2-methyl-2-propenyl-sulfonyl)-1,3,4-thiadiazolin-3-carboxylic acid-ethylester.

68. A compound according to the formula set forth in claim 1, which is 2-(dimethylcarbamoylimino)-5-methylsulfonyl-1,3,4-thiadiazolin-3-carboxylic acid-(2-propinyl)-ester.

69. A compound according to the formula set forth in claim 1, which is 2-(dimethylcarbamoylimino)-5-methylthio-1,3,4-thiadiazolin-3-carboxylic acid-2,2,2-trichloroethyl-ester.

70. A compound according to the formula set forth in claim 1, which is 2-(dimethylcarbamoylimino)-5-ethylthio-1,3,4-thiadiazolin-3-carboxylic acid-benzylester.

71. A compound according to the formula set forth in claim 1, which is 2-(dimethylcarbamoylimino)-5-isopropylthio-1,3,4-thiadiazolin-3-carboxylic acid-(2-propinyl)-ester.

72. A compound according to the formula set forth in claim 1, which is 2-(dimethylcarbamoylimino)-5-isobutylthio-1,3,4-thiadiazolin-3-carboxylic acid-(2-propinyl)-ester.

73. A compound according to the formula set forth in claim 1, which is 5-ethylthio-2-(dimethylcarbamoylimino)-1,3,4-thiadiazolin-3-carboxylic acid-(2-propinyl)-ester.

74. A compound according to the formula set forth in claim 1, which is 5-ethylsulfonyl-2-(dimethylcarbamoylimino)-1,3,4-thiadiazolin-3-carboxylic acid-benzylester.

75. A compound according to the formula set forth in claim 1, which is 5-butylsulfonyl-2-(dimethylcarbamoylimino)-1,3,4-thiadiazolin-3-carboxylic acid-butylester.

76. A compound according to the formula set forth in claim 1, which is 2-(dimethylcarbamoylimino)-5-(2-propinylthio)-1,3,4-thiadiazolin-3-carboxylic acid-methylester.

77. A compound according to the formula set forth in claim 1, which is 2-(dimethylcarbamoylimino)-5-pentylthio-1,3,4-thiadiazolin-3-carboxylic acid-benzylester.

78. A compound according to the formula set forth in claim 1, which is 2-(dimethylcarbamoylimino)-5-isobutylsulfonyl-1,3,4-thiadiazolin-3-carboxylic acid-(2-propinyl)-ester.

79. A compound according to the formula set forth in claim 1, which is 5-ethylsulfonyl-2-(dimethylcarbamoylimino)-1,3,4-thiadiazolin-3-carboxylic acid-(2-propinyl)-ester.

80. A compound according to the formula set forth in claim 1, which is 2-(dimethylcarbamoylimino)-5-pentylsulfonyl-1,3,4-thiadiazolin-3-carboxylic acid-(2-propinyl)-ester.

81. A compound according to the formula set forth in claim 1, which is 2-(dimethylcarbamoylimino)-5-pentylthio-1,3,4-thiadiazolin-3-carboxylic acid-butylester.

82. A herbicide composition comprising as its active ingredient a herbicidally effective amount of at least one compound according to claim 1 and a carrier.

* * * * *